United States Patent
Hutchins et al.

(10) Patent No.: US 6,248,514 B1
(45) Date of Patent: Jun. 19, 2001

(54) METHODS FOR MEASURING VIRAL INFECTIVITY

(75) Inventors: Beth M. Hutchins, San Diego, CA (US); Mary H. Nunnally, Highlands Ranch, CO (US); Barry J. Sugarman, San Diego, CA (US)

(73) Assignee: Canji, Inc., San Diego, CA (US)

( * ) Notice: Subject to any disclaimer, the term of this patent is extended or adjusted under 35 U.S.C. 154(b) by 0 days.

(21) Appl. No.: 09/136,327

(22) Filed: Aug. 18, 1998

Related U.S. Application Data

(63) Continuation-in-part of application No. 08/974,931, filed on Nov. 20, 1997, now abandoned, which is a continuation of application No. 08/678,485, filed on Jul. 9, 1996, now abandoned.

(51) Int. Cl.$^7$ .............................. C12Q 1/70; C12Q 3/00; C12Q 1/00; G01N 33/53
(52) U.S. Cl. ...................... 435/5; 435/3; 435/4; 435/7.1
(58) Field of Search .................................. 435/5, 3, 4, 7.1

(56) References Cited

U.S. PATENT DOCUMENTS 5,470,730 * 11/1995 Greenberg et al. ............... 435/172.3

OTHER PUBLICATIONS

Saalmuller et al.; "Rapid detection and quantification of cells infected by recombinant herpesvirus . . . "; J. Vir. Meth.; 44; pp. 99–108, 1993.*

Huyghe et al.; "Purification of a type 5 recombinant adenovirus encoding human p53 by column chromatography"; Human Gene Therapy; 6; pp. 1403–1416, 1995.*

Bauer, K.D. et al., "Analysis of Intracellular Proteins," *Methods in Cell Biology* 41:351–376 (1994).

Eyler, Y.L. et al., "Flow cytometric detection of DNA tumor virus nuclear oncogene products in unfixed cells: saponin FACS of viral oncogene products," *J. Virol. Meth.* 46:23–27 (1994).

Huyghe, B.G. et al., "Purification of a Type 5 Recombinant Adenovirus Encoding Human p53 by Column Chromatography," *Hum. Gene Ther.* 6:1403–1416 (1995).

Lynn, D.E. et al., "A BASIC Computer Program for Analyzing Endpoint Assays," *Biotechniques* 12(6):880–881 (1992).

Maizel, J.V. et al., "The Polypeptides of Adenovirus," *Virology* 36:115–125 (1968).

March, K.L. et al., "Pharmacokinetics of Adenoviral Vector–Mediated Gene Delivery to Vascular Smooth Muscle Cells: Modulation by Poloxamer 407 and Implications for Cardiovascular Gene Therapy," *Hum. Gene Ther.* 6:41–53 (1995).

Morris, T.D. et al., "Characterization of Productive and non–productive ACMNPV Infection in Selected Insect Cell Lines," *Virology* 197:339–348 (1993).

Saalmüller, A. et al., "Rapid identification and quantitation of cells infected by recombinant herpesvirus (pseudorabies virus) using a fluorescence–based β–galactosidase assay and flow cytometry," *J. Virol. Meth.* 44:33–108 (1993).

Wen, S.F. et al., "Retinoblastoma protein monoclonal antibodies with novel characteristics," *J. Immunol. Meth.* 169:231–240 (1994).

Wills, K.N. et al., "Gene therapy for hepatocellular carcinoma: Chemosensitivity conferred by adenovirus–mediated transfer of the HSV–1 thymiding kinase gene," *Canc. Gene Ther.* 2(3):191–197 (1995).

*Recombinant DNA: A Short Course*, eds. Watson, J.D. et al., W.H. Freeman and Company, New York, New York, pp. 189–190 (1983).

*Virology*, eds. Fields, B.N. et al., Raven Press, New York, New York, pp. 37–38 (1990).

* cited by examiner

*Primary Examiner*—Jeffrey Stucker
*Assistant Examiner*—Brett Nelson
(74) *Attorney, Agent, or Firm*—Towsend and Townsend and Crew LLP

(57) ABSTRACT

The instant invention addresses the need for a more accurate method of quantitating infectious viral particles in a population. The methods of the instant invention are based on the unexpected and surprising result that flow cytometry analysis of cells infected using specified ranges of viral particle concentration and/or adsorption time yields a more accurate measurement of infectious virus titer than traditional titration methods.

28 Claims, 6 Drawing Sheets

METHODS FOR MEASURING VIRAL INFECTIVITY

CROSS-REFERENCE TO RELATED APPLICATIONS

This application is a continuation-in-part of U.S. patent application Ser. No. 08/974,931, filed Nov. 20, 1997 now abandoned, which application is a continuation of U.S. patent application Ser. No. 08/678,485, filed Jul. 9, 1996 now abandoned, both of which applications are incorporated herein by reference for all purposes.

BACKGROUND OF THE INVENTION

A particular challenge in the delivery of a gene by a viral vector for therapeutic purposes is the preparation and accurate characterization of clinical dosage forms. Total particle measurement can be made by such techniques as electron microscopy of viral preparations or measurement of total DNA by optical density at 260 nm of a sodium dodecyl sulfate (SDS) treated virus suspension. However, infectivity of a viral preparation, i.e., the number of infectious viral particles in a preparation of virus, is more challenging to accurately measure.

Traditionally, infectivity particles are measured in culture by a plaque-forming unit assay (pfu) that scores the number of viral plaques as a function of dilution. An alternative to the pfu assay is the tissue culture infective dose procedure ($TCID_{50}$), which estimates infectivity as a function of intracellular staining for an antigen by direct immunofluorescence. The methods suffer from limitations including a high degree of inter-assay variability and are affected by such factors as virus replication status, vector characteristics, and virus-cell interactions.

More recently, flow cytometry or FACS (fluorescence-activated cell sorter) assays have been used to measure the number of infected cells in cell cultures infected at relatively high multiplicities of infection. For example, Saalmüller and Mettenleiter (*J. Virol. Methods* 44:99–108 (1993)) disclose the identification and quantitation of cells infected by recombinant pseudorabies virus mutants by the reaction of intracellular β-galactosidase expressed during infection with recombinant viruses with a fluorogenic substrate, followed by detection of positive cells in flow cytometry. Morris et al. (*Virology* 197(1):339–48 (1993)) studied the process of productive and non-productive recombinant AcMNPV infection in cultured cells by immunostaining cells to detect the reporter CAT gene product.

The instant invention addresses the need for a more accurate method of quantitating infectious viral particles in a population.

SUMMARY OF THE INVENTION

The present invention provides methods for determining the number of infectious virus particles in a population of virus particles. In some embodiments, the methods involve i) infecting cells in a cell population with virus particles by contacting the cells with a preparation of virus particles, ii) reacting a polypeptide expressed by the virus in infected cells with an antibody labeled with a fluorescent tag, the antibody having specificity for a polypeptide expressed by the virus; and iii) measuring immunofluorescence in the product of step (ii) by flow cytometry to determine the number of infected cells, thereby determining the number of infectious virus particles. In preferred embodiments, the virus particles contacting the cells are present at a concentration of about $2 \times 10^7$ particles/ml or less.

The methods of the instant invention are based on the unexpected and surprising result that flow cytometry analysis of cells infected at a low virus to cell ratio yields a more accurate measurement of infectious virus titer than traditional titration methods.

In another embodiment, the invention provides a method for determining the number of infectious virus particles in a population of virus particles in which the method involves: i) infecting cells in a cell population at a total particle to cell ratio of less than about 100:1 to about 0.1:1 to generate infected cells; ii) reacting a polypeptide expressed by the virus in infected cells with an antibody labeled with a fluorescent tag, the antibody having specificity for a polypeptide expressed by the virus; and iii) measuring immunofluorescence in the product of step (ii) by flow cytometry to determine the number of infected cells, thereby determining the number of infectious virus particles.

When the virus is a recombinant virus, the viral polypeptide can be encoded an exogenous gene, such as a reporter gene. In some embodiments of the invention, the exogenous gene is a tumor suppressor gene such as p53 or retinoblastoma (RB). The combinant virus can be replication competent or defective, deficient or incompetent.

In some embodiments of the invention, the virus is adenovirus. Thus, when the infected cells are cultured after infection to allow expression of a viral polypeptide, the viral polypeptide can be an adenovirus polypeptide such as hexon.

Typically the viral polypeptide is reacted with at least one antibody, although the antibody can be a mixture of antibodies. The antibody can be polyclonal or monoclonal.

DETAILED DESCRIPTION

Figure 1:
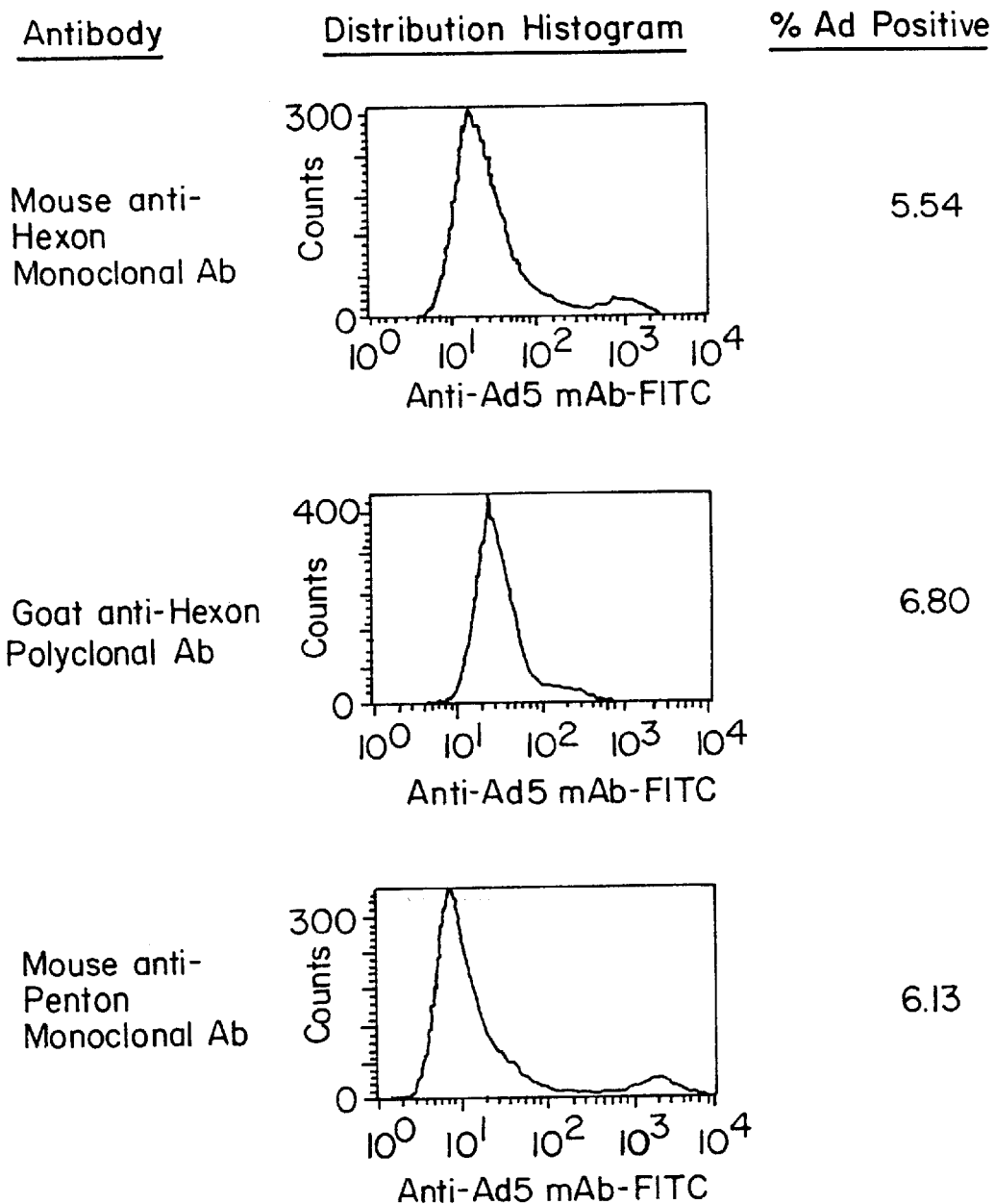
FIG. 1 shows that different anti-adenovirus antibody preparations detect similar levels of adenovirus infection. 293 cells were either mock-infected or infected with ACNRB ($5 \times 10^6$ particles/ml) and processed for flow cytometry as described in Example 2. Dilution factors used for staining with the various anti-adenovirus antibody preparations were those specified by each manufacturer. The composite above depicts the distribution of cells expressing adenovirus hexon in the sample population as well as the percentage of adenovirus infected cells in each sample population.

The present invention provides a novel flow cytometry-based analytical method that can detect the intracellular presence of adenovirus protein(s). The method is rapid (48 hours), sensitive, accurate and precise (<40% CV), rugged and broadly applicable. In one aspect of the invention, important variables are identified that affect measurement of infectious virions. These variables are both physical (initial virus particle concentration, time for adsorption of the virus to cells, length of the assay, and initial cell density) and biological (type of vector, the therapeutic transgene, and the target cell) in nature.

The assay methods provided by the invention are useful for enhancing the understanding of the underlying mechanisms of adenoviral infection, which will lead to improved vector delivery methodology. The methods are also useful for addressing issues fundamental to gene therapy, and can be used to support product development. The assay has allows reduced cycle time for bulk product and formulated material release as well as provides a method for ongoing studies with product formulation and stability. The assay methods of the invention can also be used for analysis of clinical samples for infectious adenovirus in body fluids such as serum or urine. In addition, the methods of the invention can be used to quantify neutralizing antibody titers without many of the constraints of assays in current use.

Yet another utility of the assay methods of the invention is that the methods can detect replication of replication-competent virus particles (such as, for example, adenovirus) in cell targets that do not support replication of replication deficient recombinant viral vectors (e.g., E1-deleted recombinant adenovirus). For example, one can use the assays as impurity assays for replication competent adenoviral vectors (RCA). In addition, the ability of different forms of RCA to replicate in specific cell targets can be screened using the methods of the invention.

The methods of the invention is also useful for estimating the relative infectability of any target cell population, an often overlooked but important variable to account for when evaluating transgene potency. These methods typically involve the detection of expression of a viral vector-encoded transgene protein product as a measure of infectivity. For example, a recombinant replication-deficient adenovirus encoding a gene for green fluorescent protein was used to determine relative infectability in vitro. This can be especially important for in vivo applications where one is dealing with mixed populations of cells; dosing strategies that facilitate delivery of genes to specific subpopulations of cells may be critical to achieving a therapeutic effect.

Another problem central to the development of gene delivery vehicles is identifying which is the most efficient system for a particular disease and target population. Although non-viral systems are often considered to be less effective at gene delivery at the present time, as improvements continue levels of transgene expression on a per cell basis and in a target population may increase to levels similar to viral vehicles. Quantitative cytometry methods can be used to compare transgene expression in target cell populations when using different viral and non-viral based delivery systems.

The instant invention provided methods for quantitating infectious viral particles in a population of virus particles. The term "infectious" as used herein is intended to refer to the ability of a virus to enter cells and direct the synthesis of at least one polypeptide encoded by the virus. The ability to reproduce the viral nucleic acid is not required, but is included, by this definition.

Typically, not every virus particle in a preparation is infectious. For example, particles can be damaged in preparation of the virus, thereby not affecting total particle number but decreasing the number of particles capable of infection. Furthermore, empty capsids or instability of the virus extracellularly can also contribute to the decrease in infectivity. The range of non-infectious particles to infectious particles in viral preparations can range from 1:1 to greater than 100:1. However, even non-infectious viruses can cause cytological changes or damage to exposed cells. Thus, it is advantageous to have an accurate measure of the number of infectious particles in a population so as to minimize the number of non-infectious viral particles to which cells are exposed.

Virtually any virus can be quantitated, or titered, by the methods of the instant invention, including DNA viruses, RNA viruses, replication competent viruses, replication incompetent viruses, recombinant viruses, viruses carrying transgenes, etc. Preferably, the virus can infect cells in culture. Some example of viruses amenable to this technique include, but are not limited to, adenovirus, adeno-associated virus, retrovirus, herpes simplex virus, parvovirus, Epstein Barr virus, rhinotracheitis virus, parainfluenza virus, parvovirus, bovine viral diarrhea virus, sindbis virus, baculovirus, pseudorabies virus, varicella-zoster virus, cytomegalovirus, HIV, hepatitis A, B, and C viruses, and vaccinia.

The assays involve infecting a cell line with a preparation of a viral vector particles. For example, the 293 cell line is suitable for amplification of replication-deficient recombinant adenovirus (rAd) constructs.

In some embodiments of the invention, infectivity is measured by antibodies directed against a polypeptide expressed by the virus. The polypeptide may be a structural viral polypeptide, a regulatory polypeptide, a polypeptide such as a polymerase, and so on. In some embodiments of the invention, the polypeptide is preferably expressed by an exogenous gene incorporated into the virus, such as a reporter gene. Some examples of reporter genes include β-galactosidase and chloramphenicol transacetylase (CAT). In further embodiments of the invention, the reporter gene is detected by antibodies directed against a product of the action of the reporter gene, such as the action of an enzyme on a substrate. In other embodiments of the invention, the exogenous gene is a transgene intended for therapeutic use. Some examples include but are not limited to tumor suppressor genes, including p53 or retinoblastoma (RB); interleukins, including IL-2, IL-4, and IL-10; interferons, including alpha-, beta-, and gamma interferon; other cytokines; thymidine kinase; growth factors, including GCSF and growth hormone; Factor VIII; adenosine deaminase, and so on. Typically production of polypeptide encoded by a transgene will be measured by an antibody directed against the polypeptide.

Antibodies used for detection can be polyclonal, monoclonal, or include mixtures of such antibodies. Typically, the detection is done directly by using a fluorescein-conjugated antibody directed against the viral polypeptide. However, indirect assays are also possible, in which the antibody directed against the viral polypeptide is then reacted with a fluorescein-labeled antibody. Any fluorescent label compatible with flow cytometry can be used.

In some embodiments, the assays of the invention include determining the total number of virus particles in a viral preparation. This can be measured by any of a number of traditional techniques. For example, an aliquot of a virus preparation can be prepared in a buffer containing 0.1% sodium dodecyl sulfate (SDS), after which the optical absorbance is measured at 260 nm (Maizel et al. *Virology* 36:115–125 (1968)). Total particle counts can also be obtained by preparing a sample of the viral preparation for electron microscopy, and simply counting the number of particles. A further technique for particle enumeration can include the use of anion-exchange chromatography (Huyghe et al. (1995) *Human Gene Therapy* 6:1403–1416).

Cells are then infected with dilutions of the viral preparations at total particle number to cell number ratios no higher than about 100:1, typically less than about 10:1, preferably less than about 5:1, more preferably less than about 1:1. In some embodiments the ratio is as low as about 0.1:1. Typically, at least one infection will be performed, although in some embodiments at least two parallel infections are performed at different particle to cell ratios. The cells used are typically known to be sensitive to infection by the virus. It is not required that the cells support replication by the virus, but the infection is performed under conditions that allow expression of the viral polypeptide to be detected.

The total volume of a virus preparation used to infect cells in culture is typically determined by the skilled artisan by taking into account such factors as the total number of cells to be infected, the particle concentration of the virus preparation, and the volume of the vessel in which the infection is performed. Preferably, the particle concentration of virus used to infect cells in the infection mixture is at least about $10^5$ particles per ml. In presently preferred embodiments, the concentration of viral particles in the solution used to infect the cells is about $2\times10^7$ particles per ml or less, more preferably about $10^6$ particles per ml or less, and still more preferably about $10^5$ particles per ml. The viral preparations typically are prepared under conditions favorable to stability of the virus.

Conditions for infection and, optionally, culture after infection will depend on the particular virus and the viral or reporter gene used for detection. In presently preferred embodiments, the virus particles are allowed to adsorb to the cells for at least about 5 minutes, more preferably for at least about 30 minutes, and still more preferably for at least about 1 hour. The maximum time for adsorption, in presently preferred embodiments, is about four hours. More preferably, the adsorption period is about 3 hours or less, and still more preferably the virus particles are allowed to adsorb to the cells for about 2 hours or less.

The term "culture" as used herein refers to any form of cell culture in which the minimum requirements are provided to the cells to enable continued survival for the period of interest. Thus, for example, culture can refer to preparation of a cell suspension in a suitable buffer, such as phosphate buffered saline or an incomplete growth medium, for a period of minutes or hours, or can refer cells adhering to culture dishes for minutes to days to weeks in the presence of a suitable complete growth medium. Typically, sufficient time in culture is provided for expression of the desired viral polypeptide, but preferably not enough time is provided for propagation of the infecting virus which results in further infection of cells. Thus, it is preferable that only "one round" of infection occur in these cells. In some embodiments, the length of time allowed "in culture" will be less than 1 hour to several hours. In other preferred embodiments, the length of time will be 1 to 5 days.

Typically, cells are infected under conditions favoring adsorption of the virus to the cells, although less optimal conditions can be used in some embodiments. Typically, viruses are allowed to adsorb to cells for 1–12 hours. In some embodiments, the cells are infected in a concentrated suspension with concentrated virus, to enhance the rate of infection or the number of infected cells, then diluted to a concentration more favorable for cell or viral growth. In some embodiments of the invention, it can be desirable to wash infected cells cultures to remove unabsorbed virus or components of the medium used for infection, or to expose the infected cells to media or growth conditions more favorable to their survival.

After sufficient time has elapsed to allow expression of the viral polypeptide, the cells are typically prepared as a suspension of single cells. When the cells are infected as adherent cells in tissue culture, the cultures are typically treated with a dissociating agent such as trypsin to detach the cells from the substratum. Mechanical means can also be used to detach cells, such as scraping. Cells are then collected by centrifugation and prepared in a buffer, such as incomplete or complete growth medium, for reaction with the detection reagents. Typically cells are "fixed" for immunostaining by any of a number of standard techniques. A review of the commonly used fixation techniques is provided by Bauer and Jacobberger, *Methods in Cell Biology* 41:351–376 (1994)), hereby incorporated by reference in its entirety for all purposes. When the polypeptide is detected by its activity, fluorescent reagents can be introduced into cells to allow detection of the activity, such as a fluorescein labeled substrate for an enzyme.

Infected cell populations are then subjected to analysis by standard flow cytometry, such as by the methods disclosed by Shapiro, *Practical Flow Cytometry*, 3rd ed., John Wiley and Sons (1994), hereby incorporated by reference in its entirety for all purposes. The term "FACS" is sometimes used to refer to flow cytometry, although cell sorting is not required to practice the instant invention. Typically, a minimum of about 10,000 events is acquired in the analysis. Dead cells are typically excluded from the analysis either by forward/side scatter gating or PI labelling and setting of electronic windows on the PI negative fraction. A variety of commercial software packages are available to aid in preparation and analysis of the data, such as CellQuest™. The distribution of infected and non-infected cells in the sample population is then used to calculate infectious titer.

The following examples are intended to illustrate but not limit the invention in any way.

EXAMPLE 1

In this example, ACNRB, a recombinant, replication-defective adenovirus was titered by $TCID_{50}$ and by the low particle number to cell number ratio (low ratio) method of the present invention. The exemplary virus used essentially comprised the adenovirus vector backbone disclosed by Wills et al. (*Cancer Gene Therapy* 2:191–197 (1995)) with full-length retinoblastoma cDNA inserted into the vector.

Total particle number was obtained by the "SDS/OD$_{260}$" method and anion exchange chromatography methods described above. In both assays the measured total particle concentration was $1.0 \times 10^{12}$/ml.

Infectious particles were titered by TCID$_{50}$ assay as described by Huyghe et al. (*Human Gene Therapy* 6:1403–1416 (1995)). In brief, 293 cells were plated into a 96-well microtiter plate: 100 μl of $5 \times 10^5$ cells/ml for each well in complete MEM (10% bovine calf serum; 1% glutamine) media (GIBCO BRL). In a separate plate, a 2501-μl aliquot of virus sample diluted 1:10$^6$ was added to the first column and was serially diluted two-fold across the plate. Seven rows were used for samples. One row was used for a negative control. A 100-μl aliquot of each well was transferred to its identical position in the 293 seeded plate and allowed to incubate a 37° C. in a humidified air/7% CO$_2$ incubator for 2 days. The media was then decanted by inversion and the cells fixed with 50% acetone/50% methanol. After washing with PBS, the fixed cells were incubated for 45 minutes with a FITC-labeled anti-Ad5 antibody (Chemicon International #5016) prepared according to the kit instructions. After washing with PBS, the plate was examined under a fluorescent microscope (490 mm excitation, 520 mm emission) and scored for the presence of label.

The titer was determined using the Titerprint Analysis program (Lynn, *Biotechniques* 12:880–881 (1992)).

The low ratio assay was performed as follows. $1 \times 10^6$ 293 cells (human embryonic kidney cells, ATCC CRL 1573) were seeded per well on 4 6-well dishes. The final volume per well was 1 ml. After about 2 hr, the medium (Dulbecco's modified Eagle's medium (DME high glucose) containing 4500 mg/ml D-glucose, supplemented with 5% defined, iron-supplemented bovine calf serum, 2 mM L-glutamine, and 1 mM sodium pyruvate) in each well was aspirated and replaced with 1.1 ml of medium (without serum) containing diluted virus. Adsorption was allowed to occur for 60 minutes, after which an additional 2 ml of virus-free medium was added to each well. After about 42 hr, the infected cells cultures were processed for flow cytometry analysis.

The cells were detached from the plastic substratum with a trypsin-EDTA solution (GIBCO-BRL). Detached cells were collected from each well and centrifuged at about 200×g for 10 minutes at room temperature. The supernatants were removed and the cells washed in Dulbecco's phosphate buffered saline (D-PBS) without calcium or magnesium salts. Pelleted cells were then resuspended in 2 ml cold acetone:methanol (1:1) fixative, then held on ice for 15 minutes. 7 ml D-PBS without calcium or magnesium salts was added to each tube, after which the cells were resuspended in D-PBS with 1% (v/v) calf serum. After repeating these last two steps, cells were resuspended in 50 μl D-PBS with 1% calf serum. 70 μl anti-adenovirus antibody conjugated with FITC (Chemicon #5016) in 2.0 ml D-PBS was added to each tube. The samples were incubated at 37° C. for about 50 minutes. The samples were then transferred to flow cytometry analysis tubes, diluted slightly with 0.5 ml D-PBS, and analyzed by flow cytometry. A Becton-Dickinson FACScan™ Flow Cytometer System, PN 34011570, 12-00189-01 with FACStation (MAC QUADRA 650 computer, monitor, and printer) was used with CellQuest™ Software.

The results are shown in Table 1. By the traditional TCID$_{50}$ assay, the total particle number to infectious unit ratio was 63:1. As is evident in the table, as the total particle number to cell number ratio decreased, the calculated total particle number: infectious unit ratio also decreased to as low as 12:1, thereby providing a value for infectious titer that was about 5-fold higher than the traditional assay. Thus, this low ratio assay provides an unexpectedly better (i.e. much more accurate) enumeration of the number of infectious particles in a viral preparation than traditional methods for titration. The consequences of such accurate measurements proved by the instant invention are especially important in calculating the effective doses of recombinant viruses for therapeutic use.

TABLE 1

INFECTIOUS TITER DETERMINATION:

| Total Particle to Cell Ratio | Ratio of TCID$_{50}$ Infectious Units to Cells | Virus Concentration (Particle No./mL) | % Positive Cells | Calculated Titer (IU/mL) | Mean Calculated Titer (IU/mL) | Particle No. to Infectious Titer Ratio |
|---|---|---|---|---|---|---|
| 18.9 | 0.300 | $6.5 \times 10^6$ | 31.0 | $1.6 \times 10^{10}$ | $1.87 \pm 0.31 \times 10^{10}$ | 53:1 |
|  |  | $18.3 \times 10^6$ | 37.0 | $1.8 \times 10^{10}$ | (16.6%) |  |
|  |  | $40.0 \times 10^6$ | 43.0 | $2.2 \times 10^{10}$ |  |  |
| 3.78 | 0.060 | $1.3 \times 10^6$ | 12.0 | $3.0 \times 10^{10}$ | $3.15 \pm 0.21 \times 10^{10}$ | 32:1 |
|  |  | $3.7 \times 10^6$ | 13.0 | $3.3 \times 10^{10}$ | (6.7%) |  |
|  |  | $8.0 \times 10^6$ | na | na |  |  |
| 0.756 | 0.012 | $0.26 \times 10^6$ | 5.8 | $7.3 \times 10^{10}$ | $8.67 \pm 1.18 \times 10^{10}$ | 12:1 |
|  |  | $0.74 \times 10^6$ | 7.5 | $9.4 \times 10^{10}$ | (13.6%) |  |
|  |  | $1.6 \times 10^6$ | 7.4 | $9.3 \times 10^{10}$ |  |  |

Calculated Titer (TCID$_{50}$ Assay) $1.6 \times 10^{10}$ IU/mL
Particle No. Concentration $1.0 \times 10^{12}$ PN/mL
PN:IU Ratio 63:1

EXAMPLE 2

This Example describes a study directed to identifying and optimizing those parameters critical to the measurement of infectious viral particles and to ensuring that the assay is generally applicable to all types of adenovirus preparations. The results indicate that the most important variables affecting the measurement of infectious virions are initial particle concentration, time for adsorption of the virus, and length of the assay. The results also demonstrate that one can determine virus infectivity by measuring the fraction of cells in a sample population that express a vector-associated gene. This is significant because it enables one to assess infectivity of recombinant adenovirus preparations on targets without using reporter constructs, and allows one to directly compare the transduction efficiency of different gene therapy modalities.

Materials and Methods

Cells and Cell Culture

All of the cell lines were obtained from the American Type Culture Collection (Gaithersburg, Md.). Each cell line was cultured using the media specified by the ATCC in humidified air/7% $CO_2$ incubators set at 37° C. All of the media and media supplements, with the exception of the fetal bovine sera from Hyclone (Logan, Utah), were purchased from GIBCO (Gaithersburg, Md.).

Virus Constructs and Virus Preparations

The recombinant adenovirus E1-deleted vectors chosen for these studies were all similar to ACN53, a virus containing the 1.4 kb full-length p53 cDNA with expression driven from the human cytomegalovirus promoter (Wills et al. (1994) Human Gene Ther. 5: 1079–1088). ACNRB was a construct which encodes $p110^{RB}$ in place of p53; ACNRB34 was a construct with partial deletions in both the E3 and E4 domains that also expresses RB protein; ACBGL was a construct that expresses a gpt/trpS/lacZ fusion product that retains beta-galactosidase activity (Hall et al. (1983) J. Mol. Applied Gen. 2: 101–109); ACN34 was analogous to ACNRB34 without the RB transgene; and ACBSB34 was a construct that contains a DNA insert that does not encode a gene. Wild-type adenovirus 5 was purchased from Advanced Biotechnologies (Columbia, Md.), whereas the adenovirus 5 variant dl309 (Jones and Shenk (1979) Cell 17: 683–689) was kindly provided by Dr. Robert Schneider. Virions were grown and propagated in 293 cells using published procedures, and purified by either a three-step CsCl density gradient procedure, or by column chromatography (Huyghe et al., supra.). Characterization of particle concentration was performed using anion-exchange high pressure liquid chromatography (Shabram et al. (1997) Human Gene Ther. 8: 453–465) as well as the absorbance measurement at 260 nm in 0.1% (w/v) SDS (Maizel et al. (1968) Virology 36: 115–125).

Electron Microscopy

ACNRB34-infected 293 cells were collected by trypsinization from Cytodex-1 microcarriers taken from an $8 \times 10^6$ cell/ml culture 50 hours post-infection. Cells were then gently pelleted and fixed with 2% paraformaldehyde, 1.5% glutaraldehyde in 0.1 M cacodylate buffer, pH 7.4. The post-fixation was in 1% $OSO_4$. Samples were embedded in epoxy resins and sectioned with an LKB ultramicrotome. The sections were stained with uranyl acetate and lead citrate, and visualized on a Hitachi H12A electron microscope.

Measurement of Infectious Particles by $TCID_{50}$ 293 cells were seeded at a density of $1.6 \times 10^5$ cells/cm$^2$ in 96-well flat-bottom microtiter dishes using 100 µL of 293 cell media. Dilutions of adenovirus samples were prepared in separate 96-well plates and added to the cells to bring the final volume in each well to 200 µL. Plates containing cells with virus were subsequently incubated in a humidified air/7% $CO_2$ incubator at 37° C. for 2 days. Seven rows were used for samples while the eighth row was used as a negative control. Media was decanted and the cells fixed briefly with a 1:1 mixture of methanol and acetone. After washing with Dulbecco's phosphate-buffered saline (D-PBS), the cells were stained for 45 minutes with a FITC-conjugated murine $IgG_1$ anti-adenovirus monoclonal antibody (Chemicon). The cells were examined by microscopy using epifluorescence illumination (490 nm excitation, 520 nm emission) and scored (i.e., + or −) for the presence of virus. Infectious titer was calculated using a modification of the TiterPrint Analysis program (Lynn (1992) BioTechniques 12: 880–881).

Measurement of Infectious Particles by Flow Cytometry 293 cells were seeded at a density of $1.6 \times 10^5$ cells/cm$^2$ in 6-well dishes in 1.0 ml media. The reasons for this high density of cells were (i) to generate a confluent monolayer to ensure that virus diffusing to the bottom of the well would probably adsorb to a cell, and (ii) to minimize changes in cell proliferation during the course of the assay. Each plate was incubated overnight in a humidified air/7% $CO_2$ incubator at 37° C. to facilitate 293 cell attachment. For the virus adsorption step, growth media was gently removed from each well followed by the addition of 100 µL of the diluted virus sample and 400 µL of 293 cell media. Each plate was returned to the $CO_2$ incubator for an additional 3 hours. An additional 2 ml of 293 cell media was added and all plates were incubated for 48 hours (unless otherwise indicated). Forty-eight hours was chosen because it was the longest time for hexon expression but prior to the completion of a full viral replication cycle. To stain the cells for adenovirus capsid proteins, media was removed and the cells harvested using Trypsin/EDTA. Cells were washed with D-PBS using gentle centrifugation (120×g), resuspended in 300 µl of cold D-PBS. Cells were fixed and permeabilized for 10 minutes with cold 1:1 (v/v) methanol:acetone. Again cells were washed and resuspended in 50 µl of D-PBS with 1% (v/v) bovine calf serum. Cells were stained for 45 minutes at 37° C. with either various FITC-conjugated murine $IgG_1$ anti-adenovirus monoclonal antibody preparations, a FITC-conjugated goat anti-adenovirus polyclonal antibody preparation, or appropriate FITC-conjugated isotype binding controls. Using either a FACScan™ or FACSCalibur™ flow cytometer (Becton Dickinson), between 10000 and 50000 events were acquired in list-mode format for forward scatter (FSC), side scatter (SSC), and FITC fluorescence (FL-1) parameters. Data were analyzed using Cell Quest™ cytometry software (Becton Dickinson). The percentage of adenovirus positive cells in each sample was used to determine the infectious titer.

Measurement of Transgene Expression by Flow Cytometry

SaOS-2 cells were seeded at a density of $1.0 \times 10^5$ cells/cm$^2$ in 6-well dishes in 1.0 mL of SaOS-2 cell media. They were then infected, cultured, fixed and stained as described in the preceding section with the following exceptions. For detection of the p110RB transgene product, cells were fixed and permeabilized for 10 minutes with 3 ml of cold (−20° C.) 70% (v/v) ethanol, not stained for adenovirus hexon, but rather were stained using a FITC-conjugated anti-p110RB murine monoclonal antibody, 3C8 (Wen et al. (1994) J. Immunol. Meth. 169: 231–240). A FITC-conjugate $IgG_{2a}$ isotype control was used to adjust for non-specific binding in p110RB experiments. For detection ofp53 expression, cells were fixed as described for the infectivity assay, not stained for adenovirus hexon, but stained using a PE-labeled anti-p53 murine monoclonal antibody (PharMingen). A PE-labeled isotype control was used to adjust for non-specific binding in p53 experiments. Using either a FACScan™ or FACSCalibur™ flow cytometer (Becton Dickinson), 20000 events were acquired in list-mode format for forward scatter (FSC), side scatter (SSC), FITC fluorescence (FL-1), or Phycoerythrin (FL-2) parameters. Data were analyzed using Cell Quest™ cytometry software (Becton Dickinson). The percentage of p110RB or p53 positive cells in each sample was assessed in a manner similar to what was used for hexon expression in 293 infected cells.

RESULTS

Establishing Feasibility

Cells that support replication of recombinant adenovirus undergo a number of morphometric changes after the initial infection process. Gross alterations in cell cultures were often readily apparent. Intracellular imaging of 293 cells by electron microscopy indicated that cells infected with recombinant replication-deficient adenovirus exhibited unique arrays of adenovirus capsids. This suggested that antibody reagents to these capsid proteins would allow us to readily differentiate between naive and infected cells in a mixed population.

In initial studies, we determined whether it was feasible to assess adenovirus infectivity by flow cytometry. We defined key parameters for development: target cells expressing adenovirus E1 proteins that complement in trans corresponding deletions within recombinant adenovirus vectors, appropriate dilutions of virus preparations, methods to fix and permeabilize cells that did not compromise the viral epitope yet maintained enough cell integrity for flow analysis, a mechanism to readily discriminate infected from uninfected cells by flow cytometry, and a means to calculate the infectious titer from such data. 293 cells were chosen because they were readily available and could support the proliferation of replication-deficient adenovirus (Graham and Prevec (1991) "Manipulation of adenovirus vectors." *In Methods in Molecular Biology—Gene Transfer and Expression Protocols* vol. 7, E. J. Murray Ed. (The Humana Press Inc., Clifton N.J.), pp. 109–128). An anti-adenovirus hexon mAb was chosen to detect expression of late phase capsid proteins because of prior experience with its use in Western blots and immunohistochemical staining; the working range was determined to be between 1 and 20 µg/ml with an optimal concentration near 3 µg/ml; the time and temperature for mAb incubation were shown to be 50 minutes and 37° C., respectively. While testing various fix and permeabilization methods, which included 75% (v/v) ethanol, acetone, and a 1:1 (v/v) mixture of methanol and acetone, it was determined that flow cytometry could readily discriminate (approximately a 1 to 2 log shift in relative fluorescence intensity) uninfected and infected cells in the sample population.

The last challenge was to devise a scheme to calculate infectious titer from raw flow cytometry output. Equations used in conjunction with enumerative techniques such as the plaque forming assay include parameters such as the number of foci, dilution factor, and inoculum volume (Issacs (1957) *Advan. Virus Res.* 4: 111–158; Dougherty (1964) "Animal virus titration techniques." *In Techniques in Experimental Virology*, R J C Harris, Ed. (Academic Press, N.Y.), pp. 169–223). Since the assay described herein is also an enumerative method like the pfu assay, we were able to define the relationships between assay-specific variables (sample dilution factor and inoculum volume) as well as flow cytometry data (the fraction of adenovirus hexon positive cells). Infectious titer is the product of the following: the total number of adenovirus infected cells in the sample population, the degree to which the adenovirus sample was diluted, and the reciprocal of the inoculum volume (Equation I).

$$\text{Infectious Titer (I.U./mL)} = \frac{\text{(Number of Positive Cells)}}{\text{(Dilution Factor)(Final Cell No./Well)}} \quad \text{(I)}$$
$$\overline{\text{(Total Number of Cells)(Inoculum Volume)}}$$

This provided the impetus to further develop this method into a reliable assay for characterization of recombinant adenovirus preparations.

Specificity of the Response

The initial experiment addressed whether an anti-adenovirus mAb-FITC conjugate could selectively detect cells expressing an adenovirus epitope. 293 cells either infected with ACNRB or mock infected were processed and subdivided into two equivalent amounts. Each sample pair was stained with either a murine anti-adenovirus hexon FITC conjugate or a class matched non-specific $IgG_1$ FITC conjugate (i.e., to keyhole limpet hemocyanin, an antigen not expressed in human cell lines). Positive events were identified using a gate set >1 log beyond the uninfected population. When the fluorescence histograms for each sample were compared (Table 2) it was evident that staining with the anti-hexon mAb-FITC conjugate was specific only for cells infected with ACNRB. Uninfected cells stained with either antibody preparation and infected cells stained with the $IgG_1$ FITC conjugate yielded few (<0.5%) intensely staining cells.

TABLE 2

Specificity of mAb Binding to Recombinant Adenovirus Infected 293 Cells.

| rAd Concentration[§] (particles/ml) | mAb[†] | % Ad Positive | Infectious Titer (Infectious Units/ml) |
| --- | --- | --- | --- |
| 5.0 × 10[7] | αAd mAb-FITC | 33.8 | 2.70 × 10[10] |
| 2.5 × 10[7] | αAd mAb-FITC | 15.6 | 2.50 × 10[10] |
| Uninfected | αAd mAb-FITC | 0.11 | Not Applicable |
| 2.5 × 10[7] | Control mAb-FITC | 0.37 | Not Applicable |
| 2.5 × 10[7] | Control mAb-FITC | 0.30 | Not Applicable |
| Uninfected | Control mAb-FITC | 0.13 | Not Applicable |

[§]Particle concentrations were determined using anion-exchange high pressure liquid chromatography (Shabram et al., 1997) as well as the absorbance measurement at 260 nm in 0.1% (w/v) SDS (Maizel et al., 1968).
[†]Anti-adenovirus and isotype control antibodies were purchased from Chemicon and Becton Dickinson, respectively.

In the next experiment, we asked whether the observed response was specific for a particular murine anti-adenovirus hexon mAb preparation, or could antibodies that recognize other adenovirus capsid proteins or different anti-hexon antibodies yield a similar distribution of adenovirus infected cells in the sample population. The performance of three different classes of anti-adenovirus antibodies was examined: a murine anti-hexon monoclonal antibody FITC-conjugate (Chemicon), an ion-exchange purified goat anti-hexon polyclonal antibody conjugated with FITC (Chemicon), and a murine anti-penton monoclonal antibody FITC-conjugate (Fitzgerald). Again, 293 cells were either infected with ACNRB or mock infected and incubated for 2 days at 37° C., and prepared for flow analysis. Prior to immunostaining, sample populations were subdivided to test each antibody preparation. Results are depicted in FIG. 1. The percentage of adenovirus positive cells in the population was consistent among the different antibody preparations with an the average value of 6.0%. The most noticeable difference between antibody preparations was that the adenovirus infected subpopulation was difficult to discriminate when the polyclonal anti-hexon antibody was used, whereas both of the anti-capsid mAb preparations could readily discern between infected and uninfected cells. Substituting a mixture of anti-hexon and anti-penton mAbs for any single mAb preparation did not significantly increase the percentage of adenovirus-infected cells detected (data not shown). These results further support the premise that gating based on expression of adenovirus capsid proteins could in fact be used to quantify adenovirus infected cells in a sample population.

Finally, 293 cells infected with ACN53 were segregated by FACS sorting based upon whether they expressed adenovirus hexon. Both subpopulations were tested for the presence of adenovirus DNA using transgene-specific primers and the polymerase chain reaction amplification technique. Hexon-positive cells contained recombinant adenovirus DNA, whereas the uninfected population contained no detectable amount (data not shown). This was compelling evidence that the gating procedures used did distinguish uninfected from adenovirus infected cells.

Detection of Newly Synthesized Hexon

Figure 2A:
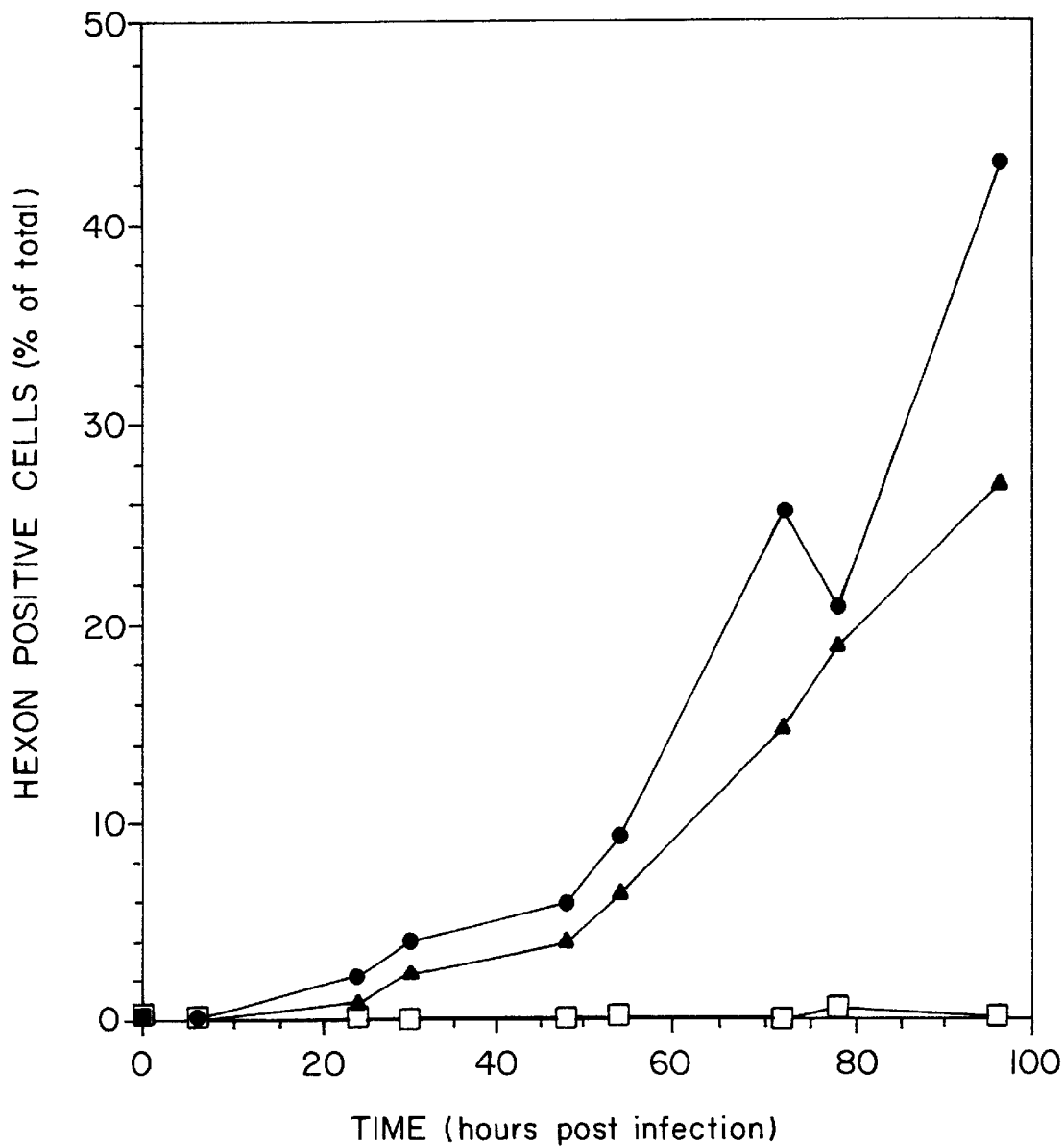
FIGS. 2A–2B show a time course for adenovirus hexon expression after infection with recombinant adenovirus. 293 cells were plated, infected with either (FIG. 2A) ACBSB34 (uninfected, open squares; $2 \times 10^6$ particles/ml filled triangles; $5 \times 10^6$ particles/ml, filled circles) or (FIG. 2B) ACN53 (uninfected, open squares; $1.5 \times 10^7$ particles/ml filled triangles; $6 \times 10^7$ particles/ml, filled circles). After 3 hours, virus was removed and replaced with fresh media. Cells were then re-incubated for specified periods of time and processed for flow cytometry. The plots depicts how the percentage of cells expressing adenovirus hexon increased in the sample population as a function of time.
Figure 2B:
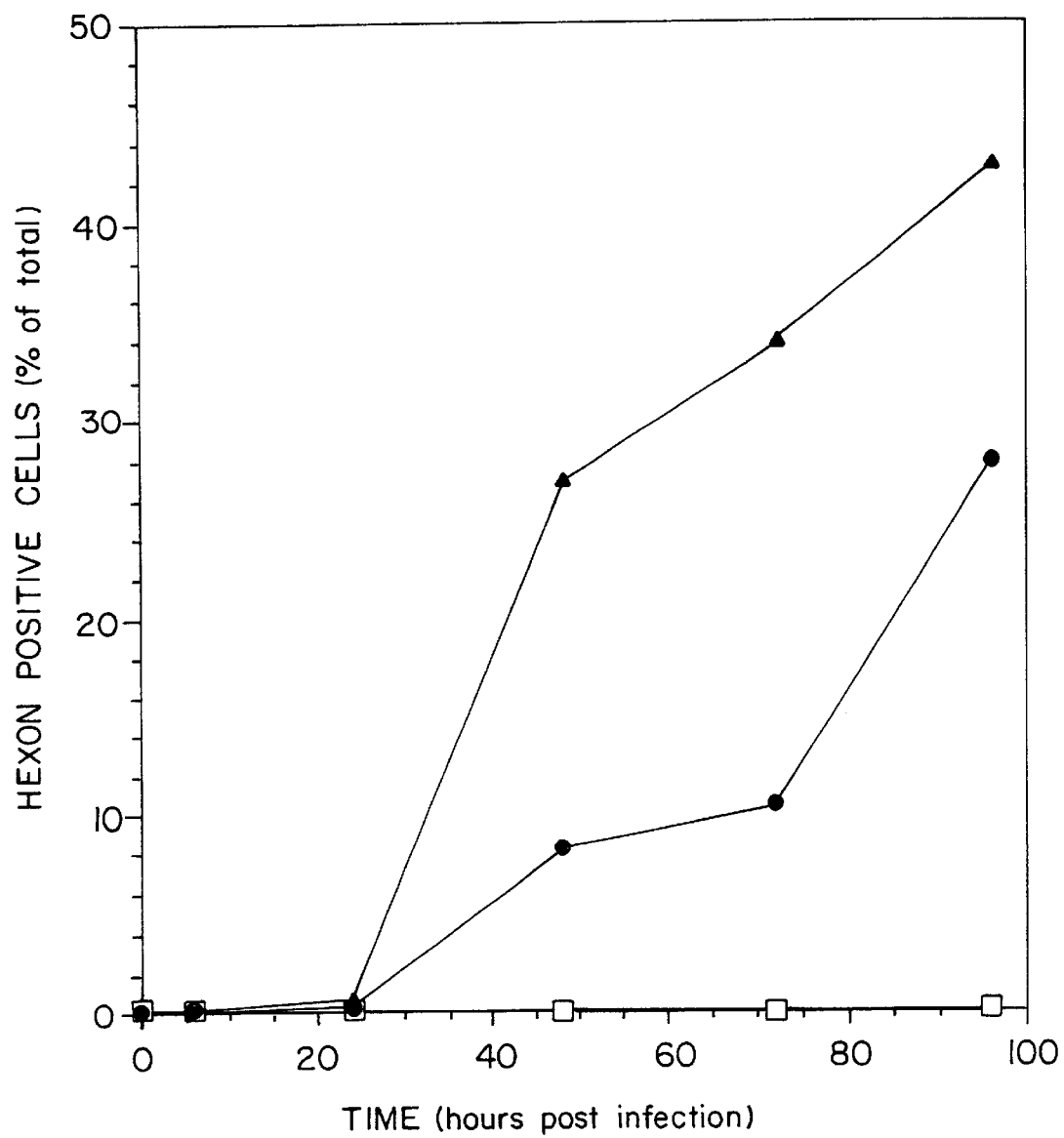

Another potential caveat was whether the adenovirus hexon protein detected within cells after immunostaining and flow analysis was due directly to the input virus used for infection or arose from newly synthesized protein as a consequence of infection. To address this concern, we designed the following experiment: treat 293 cells with either two different dilutions of a recombinant adenovirus preparation or a mock-infected control for 3 hours, remove the inoculum and replace with fresh media, and then assess sample populations at specified time points. The resulting time-course for adenovirus hexon expression in 293 cells infected with ACBSB34 is shown in FIGS. 2A–2C. Since hexon could not be detected in cells until at least 18 hours post infection, these data indicate that it arose from de novo synthesis of late phase proteins rather than from residual adenovirus particles used in the initial infection. Furthermore, the optimal window to use for assaying virus titer appears to be between 44 and 48 hours because it precedes a burst of CPE and subsequent re-infection events. Parallel time-course studies using ACNRB and ACN53 resulted in profiles of hexon expression similar to what was observed for ACBSB34, although the kinetics appeared somewhat delayed (FIGS. 2B and 2C).

Effect of Virus Particle Concentration

Figure 3:
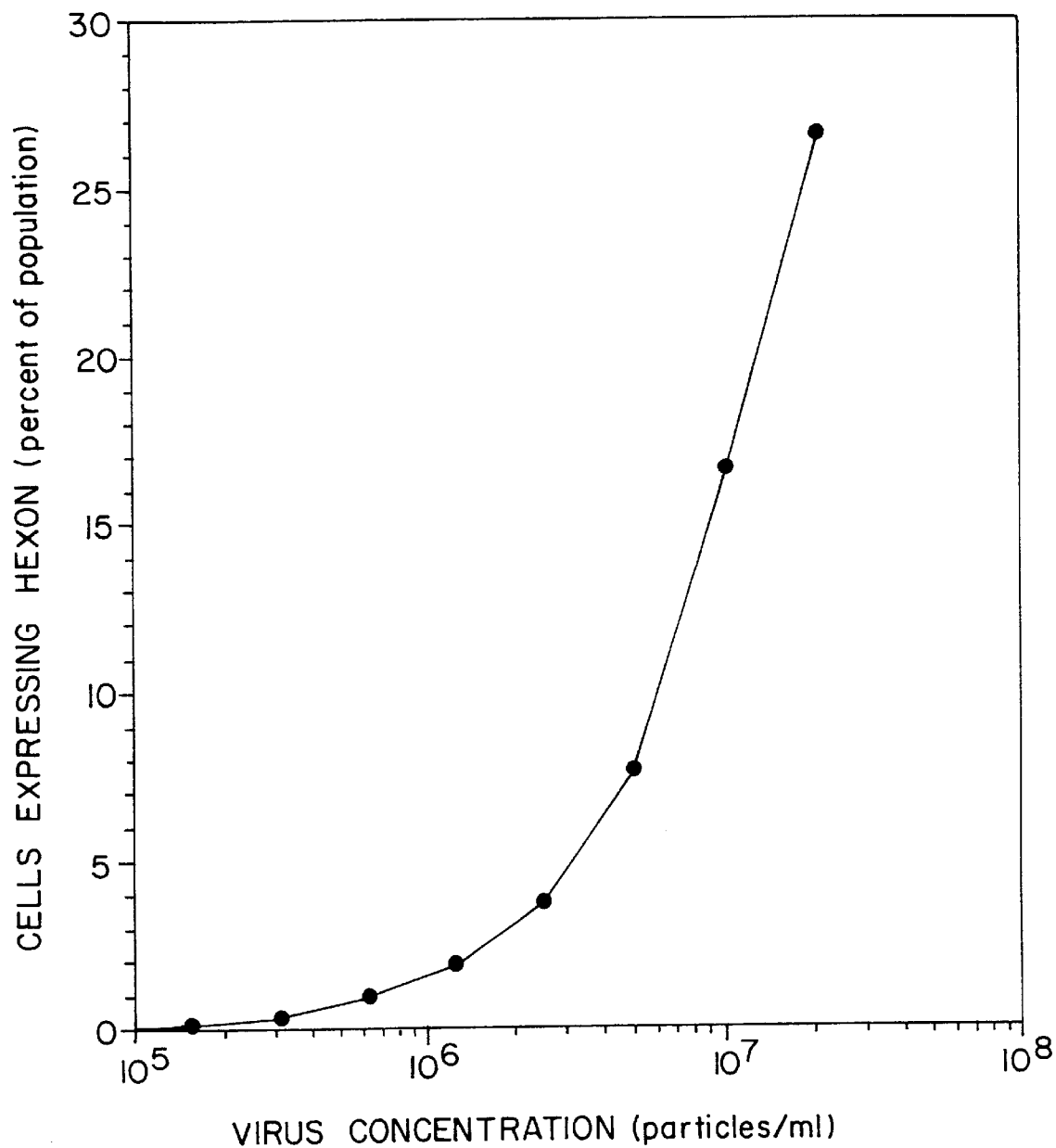
FIG. 3 shows the relationship between initial virus concentration and the percentage of cells expressing adenovirus hexon. 293 cells were plated, then infected with various concentrations of ACNRB, incubated at 37° C. for 2 days and processed for analysis by flow cytometry. The plot above depicts the distribution of adenovirus positive cells in the sample population as a function of virus concentration.

The ability of adenovirus to infect cells in vitro is limited by diffusion of particles in suspension, adsorption of particles to the cell surface, internalization of virus, and subsequent replication of viral DNA (Allison and Valentine (1959) *Biochim. Biophys. Acta.* 34: 10–23, (1959) *Biochim. Biophys. Acta.* 40: 400–410; March et al. (1995) *Human Gene Ther.* 6: 41–53; Mittereder et al. (1996) *J. Virol.* 70: 7498–7509). We therefore suspected that the initial concentration of recombinant adenovirus particles was a critical parameter affecting the determination of infectivity. A constant number of 293 cells ($1.5 \times 10^6$ per well) were infected with ACNRB using concentrations ranging from $1 \times 10^5$ to $2 \times 10^7$ particles per ml. An uninfected 293 sample was included as a negative control. After 2 days, cells were processed and analyzed by flow cytometry. The percentage of cells infected with adenovirus increased as a function of the initial virus concentration; although the detection limit was quite broad, the relationship was non-linear (FIG. 3). When the corresponding infectious titer was calculated using the values at each concentration, the relationship was essentially linear across a broad range of initial particle concentrations. The apparent difficulty in measuring the titer at low initial particle concentrations was probably due to the fact that the total number of hexon-expressing cells detected by the cytometer approached background levels; at the high end of the concentration spectrum, the drop in calculated titer was probably the result of multiple virus particles binding (and infecting) the same target cell.

Methods Validation

Prior to implementation of this assay for routine infectivity analyses, we evaluated its performance using standard validation criteria as well as to compare such results with those obtained using traditional infectivity measurements. The rationale of the study design focused on determining how reproducible and informative the resulting data were especially for distinct viral vectors with different growth characteristics.

Previous experiments showed that the dose response, i.e. the percentage of cells expressing adenovirus hexon protein as a function of initial adenovirus particle concentration, was nonlinear (FIG. 2). The range of quantitation was between $1 \times 10^5$ to approximately $2 \times 10^7$ particles/ml; the limit for infectivity was as low as 300 I.U./ml. The test for precision, a measure of assay reproducibility, was used to study three parameters: analyst to analyst, plate to plate, and day to day variability. Analyst to analyst precision was about 10% while plate to plate ranged from approximately 5 to 15% (Table 3). Inter-assay variation was 39.3% using tests conducted on four separate days. The test for robustness, which was a measure of the ability of the assay to perform reliably under a variety of conditions, compared results of two analysts over four days using different reagents, dilutions, and different batches of ACN53, ACNRB, and replication competent type 5 adenovirus. Coefficients of variation up to approximately 41% were observed (Table 4) demonstrating that the assay was robust.

TABLE 3

Precision and Accuracy of Infectious Titer Determination by FACS

| Day | Average Titer (I.U./ml) | Intra-day Variation | Inter-day Variation |
|---|---|---|---|
| 1 | $1.89 \times 10^{10}$ | 4.96% | 21.08% |
| 2 | $1.14 \times 10^{10}$ | 14.85% | 28.67% |
| 3 | $9.59 \times 10^9$ | 7.56% | 10.23% |
| 4 | $7.60 \times 10^9$ | 8.37% | 11.45% |

N=16 for all analyses.

TABLE 4

Robustness of Infectious Titer Determination by Flow Cytometry

| Recombinant Adenovirus | Number of Analyses | Average Titer (I.U./ml) | Variation |
|---|---|---|---|
| ACNRB | 11 | $3.07 \times 10^{10}$ | 40.30% |
| Wild Type Ad5 | 16 | $2.34 \times 10^{10}$ | 39.80% |
| ACN53 | 16 | $1.95 \times 10^{10}$ | 30.40% |

A second aspect to the validation process was to correlate the results observed using the FACS-based assay described herein with the $TCID_{50}$ assay for infectivity. Six different adenovirus preparations were tested in each assay using the same target cells. Although the results depicted in Table 5 show that the infectious titers determined using either assay were similar, the $TCID_{50}$ results were often quite variable (i.e., greater than 200%). Further tests using a different preparation of ACBSB34 confirmed these results and indicated that the distribution of titer results was log-normal rather than a symmetric configuration. The geometric mean (N=12) was $3.04 \times 10^{10}$ (± one standard deviation, $2.02 \times 10^{10}$ to $4.59 \times 10^{10}$) and $3.17 \times 10^{10}$ (± one standard deviation, $1.46 \times 10^{10}$ to $6.86 \times 10^{10}$) I.U./ml for the FACS-based and $TCID_{50}$ assays, respectively.

TABLE 5

A Comparison of the Infectious Titers Determined by Different Assays

| Adenovirus Construct[§] | Flow Cytometry | $TCID_{50}$ |
|---|---|---|
| ACNRB34 | $1.1 \times 10^{10}$ | $0.8 \times 10^{10}$ |
| ACNRB | $2.5 \times 10^{10}$ | $2.1 \times 10^{10}$ |
| ACN34 | $1.1 \times 10^{10}$ | $0.7 \times 10^{10}$ |
| ACN53 | $0.8 \times 10^{10}$ | $1.3 \times 10^{10}$ |
| ACBGL | $3.0 \times 10^{10}$ | $3.6 \times 10^{10}$ |
| ACBSB34 | $13 \times 10^{10}$ | $15 \times 10^{10}$ |

[§]Lot numbers for the preparations listed above were as follows: ACNRB34, lot C05; ACNRB, lot C01; ACN34, lot C01; ACN53, lot R32; ACBGL, lot R22; and ACBSB34 lot R01.

Detecting Maturation of replication-Competent Adenovirus

Figure 4:
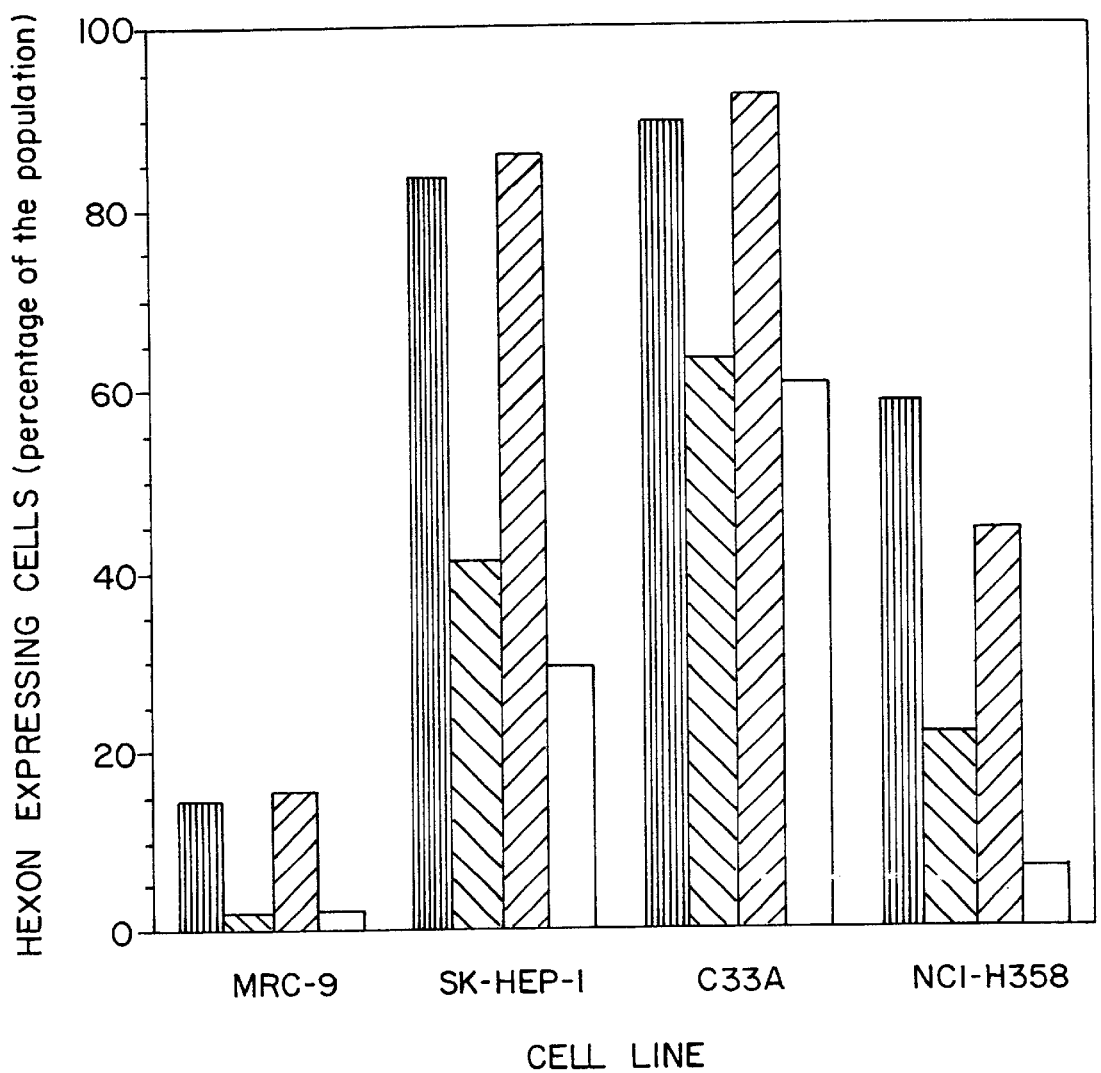
FIG. 4 shows the detection of adenovirus hexon protein in cells infected with replication-competent adenovirus. MRC-9, SK-HEP-1, C33A, and NCI-H358 cells were plated, then infected briefly with either $1.8 \times 10^9$ or $1.8 \times 10^8$ particles per milliliter of type 5 adenovirus or dl309, incubated at 37° C. for 2 days and processed for analysis by flow cytometry. A mock-infected cell control was included for each cell line. The diagram shows the percentage of adenovirus positive cells in each respective sample population. Solid and diagonal bars represent cells infected with higher and lower concentrations of type 5 adenovirus, whereas stippled and open bars represent cells infected with higher and lower concentrations of dl309.

Since wild type or replication-competent adenovirus can infect and replicate in many human cell types, it was plausible to assume that this FACS-based assay could be adapted to differentiate between infected and naive normal cell populations. In order to investigate this further, we infected various cell lines with either preparations of type 5 adenovirus or an adenovirus type 5 variant known as dl309. Using conditions similar to what was previously described for the 293-based assay, the various samples were cultured for about 2 days after infection and analyzed by FACS for expression of hexon. The data, as shown in FIG. 4, indicate that it was feasible to monitor viral infectivity using this procedure and that the response appeared to be dependent upon the initial concentration of adenovirus particles. Also, there was close agreement between the results (i.e., the percentage of cells staining positive for hexon expression) for a given cell line. These data suggested that this approach could be used to address a number of issues: (i) to compare the relative infectivity of replication-competent virus in different cell types; (ii) to develop a strategy to detect replication-competent adenovirus (RCA) in batches of replication-deficient adenovirus; and (iii) to use bivariate analyses to study coordinate expression of adenovirus hexon and specific cell surface determinants which could enable one to determine whether viral replication discriminates between subtypes of primary cells in a mixed target population.

Measurement of Gene Transduction

Figure 5A:
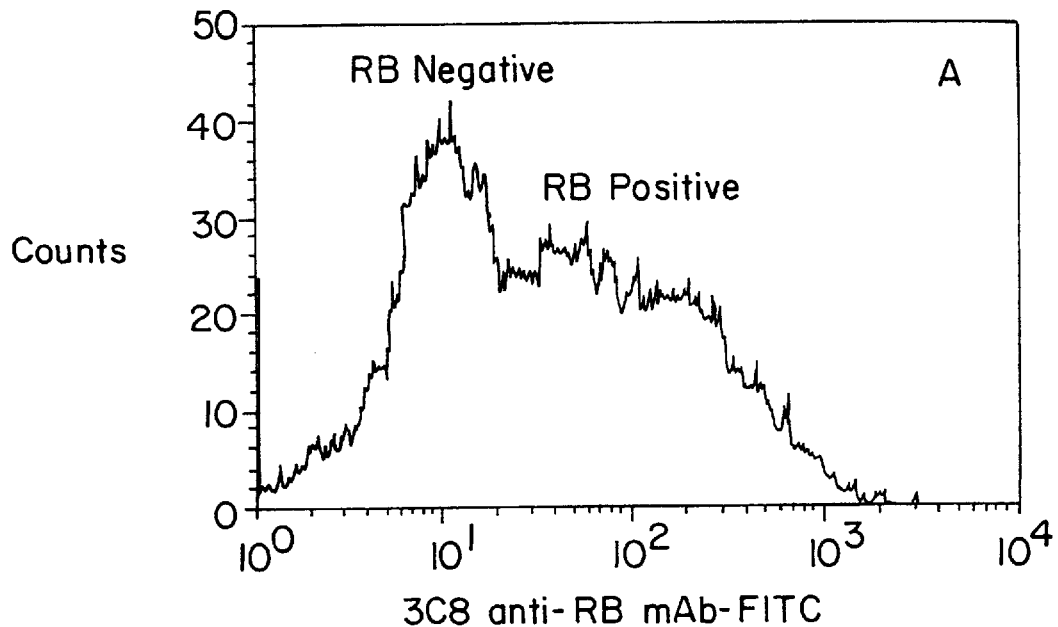
FIGS. 5A–5B show transgene expression for p110rb and p53 proteins in saos-2 cells. SaOS-2 cells were plated, then infected with either ACNRB (FIG. 5A) or ACN53 (FIG. 5B) for 3 hours, diluted, and incubated at 37° C. for 2 days. Cells were harvested, fixed and permeabilized, and stained for either p110RB or p53 expression as described in Example 2. Each plot shows the distribution of cells expressing the appropriate transgene product within the sample population.
Figure 5B:
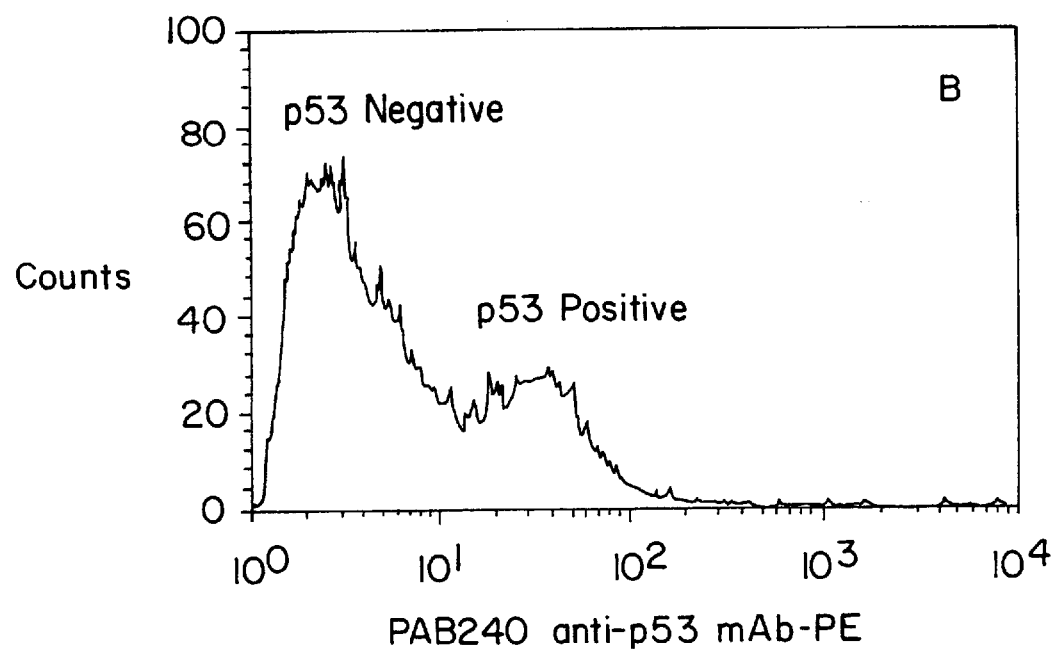

The objective of this experiment was to see whether the infectivity of a construct could be determined for different cell lines by detecting transgene expression using FACS. Usually, recombinant adenovirus constructs encoding a reporter gene such as lacZ was used to determine relative infectivity on different cell lines (Saalmuller and Mettenleiter (1993) *J. Virol. Methods* 44: 99–108; Harris et al (1996) *Cancer Gene Ther*. 3: 121–130). However, what investigators are most interested in is the infectivity of the recombinant adenovirus expressing a gene of interest rather than a control construct. SaOS-2 cells, a line that does not express normal RB protein (Goodrich and Lee (1993) *Biochim. Biophys. Acta*. 1155: 43–61), were plated and either infected with ACNRB34, ACN34, or mock infected with media alone. Two days post infection, cells were processed and stained with an anti-RB mAb FITC conjugate known as 3C8 (Wen et al. (1994) *J. Immunol. Meth*. 169: 231–240). Positive events (i.e., cells expressing RB protein) were identified within the total population (FIGS. 5A–5B). Using Equation I and a value of 46.5% for the RB positive fraction, the infectious titer of this construct on SaOS-2 cells was determined to be $3 \times 10^9$ I.U./ml, a value that was approximately 2.5-fold lower than the corresponding titer determined using 293 cells. Neither mock-infected or cells infected with the recombinant adenovirus control (i.e., ACN34) showed significant staining with 3C8 (<0.5%).

DISCUSSION

Infectious Titer by Flow Cytometry

This Example describes the development of a novel flow-cytometry based method to measure the infectious titer of recombinant adenoviral preparations. This assay is rapid, sensitive, reproducible and can be completed within three days. It is a quantitative procedure that assesses infectivity as a function of the number of cells staining positively for expression of a viral antigen in a mixed target cell population. Experimental controls such as uninfected target cells and the use of a nonspecific IgG control conjugated with FITC helped to verify the assignment of adenovirus infected cells in the cell population. Additional studies using different anti-adenovirus antibody preparations for detecting expression of viral capsid proteins yielded equivalent infectious titers and further confirmed the rationale of this approach. Since this method was sensitive to the initial conditions used for infection as well as to events occurring as a result of the infection process, results were usually higher and more precise when compared to traditional assays for infectivity. Replication-deficient recombinant adenovirus constructs with distinct replication cycles, transgenes, and backbones all behaved reliably in this flow cytometry assay. Validation studies demonstrated that the assay was precise and robust for use in bulk product and formulated material release.

Implications for Gene Therapy

One of the primary reasons why infectious titer assays gained general acceptance in virology was that they were the only methods which allowed investigators to "quantify" infectious particles in batches of either purified virus or in cell lysates. Data using these assays led to the development of two paradigms in adenovirus biology: that most particles present in adenovirus preparations are not infectious, and that multiplicity of infection (MOI)—the ratio of infectious units to target cells—is an appropriate unit for dosing in vitro and in vivo.

The data presented herein strongly suggest that neither hypothesis is correct. The first tenet was based upon infectious titer data and circular reasoning. Unfortunately, infectious titer assays are often imprecise and detect only a small percentage of the particles in solution because the infection process is itself diffusion limited (Allison and Valentine, 1959a, 1959b, supra.; March et al. supra.; Nyberg-Hoffnan et al. (1997) *Nature Medicine* 3: 808–811).

The second assumption, that MOI is an appropriate dosing unit, is also not valid. There are obvious practical limitations. MOI is inherently variable because it is a ratio of two imprecise values. It does not account for the volume used to administer a sample and thus yields no information about critical parameters such as particle concentration and time of adsorption. Furthermore, the target cell number can never be determined but only estimated in vivo. Since particle concentration can be accurately determined using either spectrophotometric or chromatographic techniques, the regulatory recommendation that the gene therapy community base clinical dosage forms on total particles is advisable (*Guidance for Human Somatic Cell Therapy and Gene Therapy*, CBER, 1998 (www.fda.gov/cber/gdlns/somgen.txt).

All references cited herein are expressly incorporated by reference in their entirety for all purposes.

What is claimed is:

1. A method of determining the ratio of total virus particles to infectious virus particles in a viral preparation, the method comprising:
   a) determining the number of infectious virus particles in the viral preparation by a method that comprises:
      i) infecting cells in a cell population with virus particles by contacting the cells with a portion of the viral preparation, wherein the virus particles contacting the cells are present at a concentration of about $2 \times 10^7$ particles/ml or less;
      ii) reacting a polypeptide expressed by the virus particles in infected cells with an antibody labeled with a fluorescent tag, the antibody having specificity for a polypeptide expressed by the virus; and
      iii) measuring immunofluorescence in the product of step (ii) by flow cytometry to determine the number of infected cells, thereby determining the number of infectious virus particles in the portion of the viral preparation;
   b) determining the total number of virus particles in the portion of the viral preparation; and
   c) calculating the ratio of total virus particles to infectious virus particles in the viral preparation.

2. The method of claim 1, wherein the concentration of virus particles is about $10^6$ particles/ml or less.

3. The method of claim 2, wherein the concentration of virus particles is about $10^5$ particles/ml.

4. The method of claim 1, wherein the concentration of virus particles is about $10^5$ particles/ml or greater.

5. The method of claim 1, wherein the cells are contacted with the preparation of virus particles for at least about five minutes.

6. The method of claim 5, wherein the cells are contacted with the preparation of virus particles for at least about thirty minutes.

7. The method of claim 5, wherein the cells are contacted with the preparation of virus particles for at least about one hour.

8. The method of claim 1, wherein the cells are contacted with the preparation of virus particles for about four hours or less.

9. The method of claim 8, wherein the cells are contacted with the preparation of virus particles for about three hours or less.

10. The method of claim 8, wherein the cells are contacted with the preparation of virus particles for about two hours or less.

11. The method of claim 1, wherein the cells are fixed after infecting the cells with the virus particles.

12. The method of claim 1, wherein the cells are present as a confluent monolayer on a surface of a container in which the infection step is performed.

13. The method of claim 12, wherein the container is a well of a microtiter plate.

14. The method of claim 12, wherein the cells are seeded into the container at a density of about $10^5$ cells/cm$^2$.

15. The method of claim 1, wherein the virus is adenovirus.

16. The method of claim 15, wherein the viral polypeptide is hexon.

17. The method of claim 1, wherein the cells are cultured after infection to allow expression of the viral polypeptide.

18. The method of claim 1, wherein the virus is a recombinant virus.

19. The method of claim 1, wherein the viral polypeptide is encoded by an exogenous gene.

20. The method of claim 19, wherein the exogenous gene is a reporter gene.

21. The method of claim 19, wherein the exogenous gene is p53.

22. The method of claim 19, wherein the exogenous gene is retinoblastoma.

23. The method of claim 1, wherein the antibody is a mixture of antibodies.

24. The method of claim 1, wherein the antibody is polyclonal.

25. The method of claim 1, wherein the antibody is monoclonal.

26. The method of claim 1, wherein the virus is replication defective.

27. The method of claim 1, wherein the virus particles are selected from the group consisting of adenovirus, adeno-associated virus, retrovirus, herpes simplex virus, parvovirus, Epstein Barr virus, rhinotracheitis virus, parainfluenza virus, parvovirus, bovine viral diarrhea virus, sindbis virus, baculovirus, pseudorabies virus, varicella-zoster virus, cytomegalovirus, HIV, hepatitis A, B, and C viruses, and vaccinia virus.

28. The method of claim 27, wherein the virus particles are adenoviral particles or retroviral particles.

* * * * *